United States Patent
Moszner et al.

(10) Patent No.: US 6,350,839 B2
(45) Date of Patent: Feb. 26, 2002

(54) HYDROLYSIS-STABLE AND POLYMERIZABLE ACRYLOPHOSPHONIC ACID MONOESTERS

(75) Inventors: Norbert Moszner, Eschen; Frank Zeuner; Volker Rheinberger, both of Vaduz, all of (LI)

(73) Assignee: Ivoclar Vivadent AG (LI)

( * ) Notice: Subject to any disclaimer, the term of this patent is extended or adjusted under 35 U.S.C. 154(b) by 0 days.

(21) Appl. No.: 09/835,751

(22) Filed: Apr. 16, 2001

Related U.S. Application Data

(60) Provisional application No. 60/250,711, filed on Dec. 1, 2000.

(30) Foreign Application Priority Data

Apr. 17, 2000 (DE) .......................... 100 18 969

(51) Int. Cl.[7] .............................. C08F 230/02
(52) U.S. Cl. ...................... 526/278; 526/274; 526/277; 523/116; 523/118
(58) Field of Search ................. 526/274, 277, 526/278; 523/116, 118

(56) References Cited

U.S. PATENT DOCUMENTS 4,650,591 A    3/1987   Boothe et al. ............. 210/700

FOREIGN PATENT DOCUMENTS

| DD | 273 846 A1 | 11/1989 |
|----|------------|---------|
| DE | 27 11 234 B2 | 9/1977 |
| DE | 3210775 A1 | 9/1983 |
| DE | 3313819 A1 | 10/1984 |
| DE | 197 46 708 A1 | 4/1999 |
| EP | 0 089 654 A3 | 3/1984 |

*Primary Examiner*—Helen L. Pezzuto
(74) *Attorney, Agent, or Firm*—Nixon Peabody LLP

(57) ABSTRACT

Hydrolysis-stable and polymerizable acrylophosphonic acid monoesters with the general formula (I)

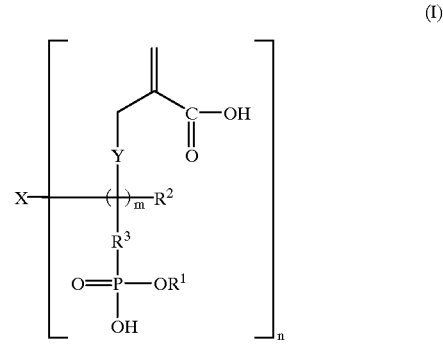

which are particularly suitable as a component of dental materials are disclosed.

10 Claims, No Drawings

HYDROLYSIS-STABLE AND POLYMERIZABLE ACRYLOPHOSPHONIC ACID MONOESTERS

This application claims the benefit of U.S. Provisional Patent Application No. 60/250,711, filed Dec. 1, 2000, which is herein incorporated by reference in its entirety.

The present invention relates to polymerizable acrylophosphonic acid monoesters which have a high hydrolytic stability and are suitable in particular for preparing, or as components of, polymers, adhesives or other materials and mainly dental materials.

Polymerizable phosphonic acids are of polymer-chemical importance mainly as comonomers. They allow the preparation of organic polymers with high thermal stability, good adhesion properties, high ignition temperature and good solubility in polar solvents. For this purpose, numerous monomeric phosphonic acids with polymerizable vinyl, dienyl, allyl, or styryl groups have been synthetized and polymerized. An overview of phosphonic acids is given by Houben-Weyl, Methoden der Organischen Chemie, Vol. E 20 ($2^{nd}$ part), Georg Thieme Verlag, Stuttgart-New York 1987, p. 1300 et seq). Examples of such conventional polymerizable phosphonic acids are vinyl phosphonic acid, allylbenzene phosphonic acid, α-aminoallyl phosphonic acid, phenylethene phosphonic acid, 1,3-butadiene or isoprene phosphonic acid, 4-vinylbenzene phosphonic acid or 2-(4-vinylphenyl)-ethane phosphonic acid.

Phosphonic acids in which the C=C group is bound to the phosphorus atom directly or via an oxygen atom, such as e.g. vinyl phosphonic acid or ethyl phosphonic acid monovinyl ester, show only a moderate tendency towards homopolymerization, so that only homopolymers with a low molecular weight are accessible.

High-molecular-weight polymerisates can on the other hand be obtained from (meth)acrylophosphonic acids or esters in which the (meth)acrylic group is not bound directly to the phosphorus, but via a hydrolysis-stable spacer group. Such (meth)acrylophosphonic acid derivatives are described for example in DE-B-27 11 234.

DE-A-32 10 775 discloses 2-acrylamido-2-methyl-propane phosphonic acid with the formula $CH_2=CH-CONH-C(CH_3)_2-CH_2-P(=O)(OH)_2$ as well as its use for preparing copolymerides.

DE-A-33 13 819 and JP 62-63314 (Chem. Abstr. 107 (1987), 41318f) disclose methacrylic acid-(2-phosphono-1,1-dimethylethylamine) of the formula $CH_2=C(CH_3)-CONH-C(CH_3)_2-CH_2-P(=O)(OH)_2$.

According to EP-B-0 089 654 and U.S. Pat. No. 4,650,591 acrylic acid-(2-phosphono-1,1-dimethylethylamine), also called 2-acrylamido-2-methylpropylphosphonic acid, is suitable as a corrosion inhibitor in the form of its homo- or copolymers.

DD-A-273 846 discloses adhesion promoters based on N-acyl-aminomethan-bisphosphonic acid derivatives.

These known (meth)acrylophosphonic acid derivatives are not stable in aqueous solution. Rather, they show a hydrolytic clearage of the (meth)acrylic group which is even catalyzed by dissociated protons of the phosphonic acid group and thus accelerated.

The use of aqueous solutions is however advantageous or absolutely necessary in a whole series of applications of polymerizable phosphonic acids. This is the case e.g. in the preparation of low viscosity adhesives which are free from organic solvents, or in dental adhesives which lead to an optimal wetting of the moist dentine surfaces only in aqueous form.

DE 197 46 708 A1 discloses polymerizable acrylophosphonic acids which are hydrolysis-stable in an aqueous solution, have good adhesion properties, can be polymerized with conventional radical initiators and are therefore suitable as a component in particular of adhesives, molded articles, cements or composites and in particular dental materials. The acrylophosphonic acids show a good solubility, in the form of their carboxylic acid esters, in water and polar organic solvents, whereas in the form of carboxylic acids they are easily soluble in water but hardly soluble in organic solvents. The different dissolving behaviour of ester and acid can be disadvantageous in the case of aqueous materials. The hydrolysis of the carboxylic acid esters to produce the free carboxylic acid and alcohol can significantly change the solubility of the monomers and thus lead to partial or complete precipitation of the phosphonic acid component and thus influence the properties of the material.

The object of the invention is the preparation of hydrolysis-stable polymerisable acrylophosphonic acid derivatives which are easily soluble in water and in polar organic solvents and the solution behaviour of which is not changed by hydrolysis.

Surprisingly, this object was achieved by acrylophosphonic acid esters of the following general formula (I)

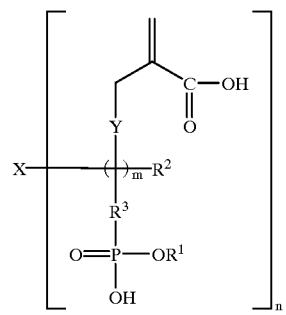

in which $R^1$, $R^2$, $R^3$, X, Y, m and n, independently of each other, have the following meanings:

$R^1$=a linear or branched $C_1$ to $C_{20}$ alkyl or $C_6$ to $C_{14}$ aryl radical;

$R^2$=hydrogen, a linear or branched $C_1$ to $C_5$ alkyl or phenyl radical;

$R^3$=a linear or branched $C_1$ to $C_8$ alkylene radical, phenylene or is absent;

Y=oxygen, $C_1$ to $C_8$ alkylene or is absent;

m=0 or 1;

n=1 or 2;

provided that Y=O, m=0 and $R^3$=absent cannot be true at the same time and further provided that for m=1 and n=1

X=hydrogen or a linear or branched $C_1$ to $C_5$ alkyl radical or a $C_6$ to $C_{14}$ aryl radical;

for m=1 and n=2

X=a linear or branched $C_1$ to $C_{10}$ alkylene, $C_6$ to $C_{10}$ arylene, $C_7$ to $C_{20}$ arylalkylene radical or a chemical bond which links together two radicals with the structure of formula (I) in brackets.

The individual alkyl and alkylene radicals can be linear, branched or cyclic. In addition, the individual alkyl, aryl, alkylene, arylene, phenyl, phenylene and arylenealkylene radicals have one or more, preferably 1 to 2 substituents, such as Cl, Br, $CH_3$, COOH, CN or preferably OH.

$R^1$ is preferably unsubstituted or substituted by one or more OH groups, preferably 1 or 2 OH groups. The remaining radicals are preferably not substituted.

Further, there are preferred definitions for the above-mentioned variables of the formula (I) which, unless otherwise stated, can be chosen independently from each other and are as follows:

$R^1$=a linear or branched $C_1$ to $C_{10}$ alkyl or phenyl radical;

$R^2$=hydrogen or a linear or branched $C_1$ to $C_3$ alkyl radical;

$R^3$=a linear or branched $C_1$ to $C_4$ alkylene radical, phenylene or is absent;

Y=oxygen or is absent;

X=hydrogen or a linear or branched $C_1$ to $C_3$ alkyl radical (for m=1 and n=1); or X=a linear or branched $C_1$ to $C_6$ alkylene radical, phenylene or a chemical bond which links together two radicals with the structure of formula (I) in brackets (for m=1 and n=2).

Meanings which are particularly preferred and likewise chosen independently of each other are:

$R^1$=a linear or branched $C_1$ to $C_4$ alkyl radical which is unsubstituted or can be substituted by an OH group;

$R^2$=hydrogen or a linear or branched $C_1$ to $C_3$ alkyl radical;

R=a linear or branched $C_1$ to $C_4$ alkylene radical, phenylene or is absent;

Y=oxygen or is absent.

Furthermore, acrylophosphonic acid monoesters are particularly preferred in which $R^1$, $R^2$, $R^3$, Y and n have the above mentioned meanings and (i) m=0 or (ii) m=1, n=2 and x=phenylene or a chemical bond which links together the two radicals with the structure of formula (I) in brackets.

Preferred compounds are those where at least one, particularly preferably all, of the variables of formula (I) have the preferred definitions described above, the formula (I) including all the stereoisomers possible through the named substituents and their mixtures, such as racemates.

If m is equal to 0, the radicals X and $R^2$ are absent.

The acrylophosphonic acid monoesters (APME) according to the invention of the formula (I) can be prepared by partial hydrolysis of corresponding acrylophosphonic acid esters APE. For this, diluted caustic soda solution can be used, a silylation for example with trialkylsilanes is not necessary, so that the acrylophosphonic acid monoesters are more easily and economically accessible than comparable phosphonic acids.

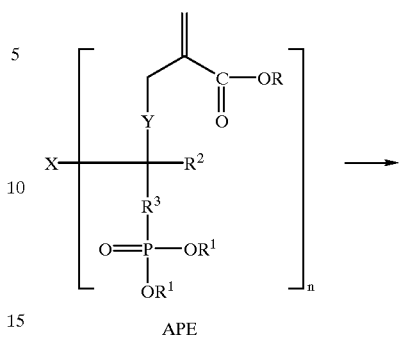

APE

APME

Specifically, the reaction of 2-[4-(dimethoxyphosphoryl)-2-oxa-butyl]-acrylic acid ethyl ester with caustic soda solution results in the corresponding phosphonic acid monoester (2-[4-hydroxymethoxyphosphoryl-2-oxa-butyl]-acrylic acid):

The acrylophosphonic acid esters (APE) used for this can be obtained for example by reacting α-halogen methylacrylic acid esters (HMAE; U=halogen, preferably Cl or Br) with mono- or difunctional phosphonic acid esters (PE) using methods known from organic chemistry for preparing C—C, C—O or C—S bonds (cf. C. Weygand, G. Hilgetag, Organisch-chemische Experimentierkunst, Johann Ambrosius Bart Verlag, Leipzig 1970, pp. 963 et seq., 362 et seq., and 657 et seq; N. Moszner, F. Zeuner, U.K. Fischer, V. Rheinberger, Macromol. Chem. Phys. 200 (1999) 1062). This reaction can be illustrated by the following general reaction equation:

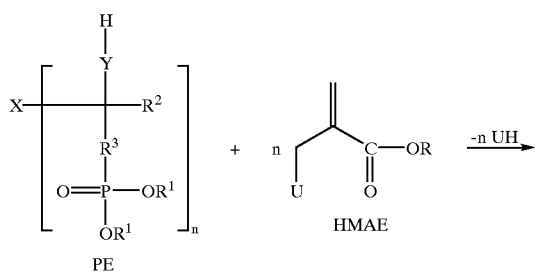

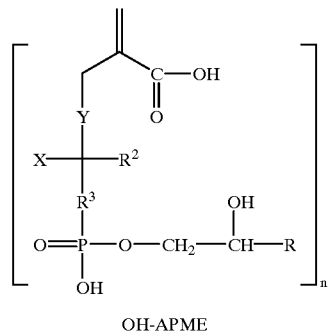

Specifically, the reaction of α-chloromethylacrylic acid ethyl ester with 2-hydroxyethylphosphonic acid dimethylester gives 2-[4-(dimethoxyphosphoryl-2-oxa-butyl]-acrylic acid ethyl ester:

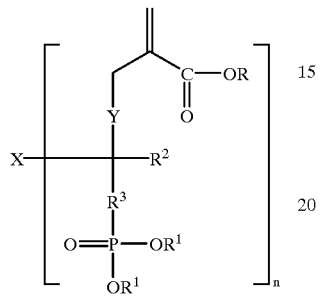

A further preparation possibility is the reaction of corresponding acrylophosphonic acid (APA) with epoxides accompanied by formation of OH-substituted acrylophosphonic acid monoesters OH-APME. The reaction can be carried out analogously to B. Costisella, H. Gross, J. Prakt. Chem. 317 (1975) 798.

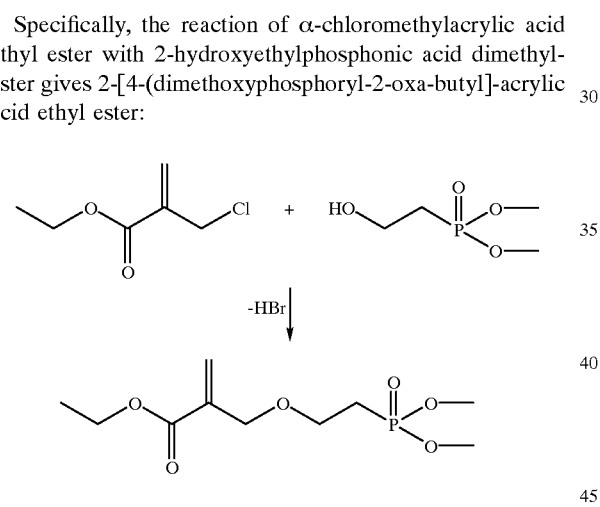

Specifically, the reaction of 2-[4-dihydroxyphosphoryl-2-oxa-butyl]-acrylic acid with propylene oxide results in the corresponding phosphonic acid monoester (2-{4-[hydroxy-(2-hydroxypropoxy)]-phosphoryl-2-oxa-butyl}-acrylic acid):

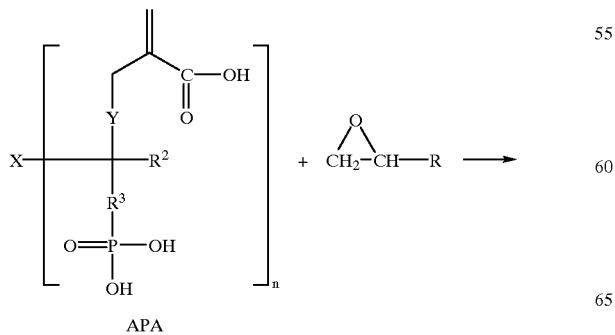

Examples of the acrylophosphonic acids according to the invention of formula (I) are inter alia:

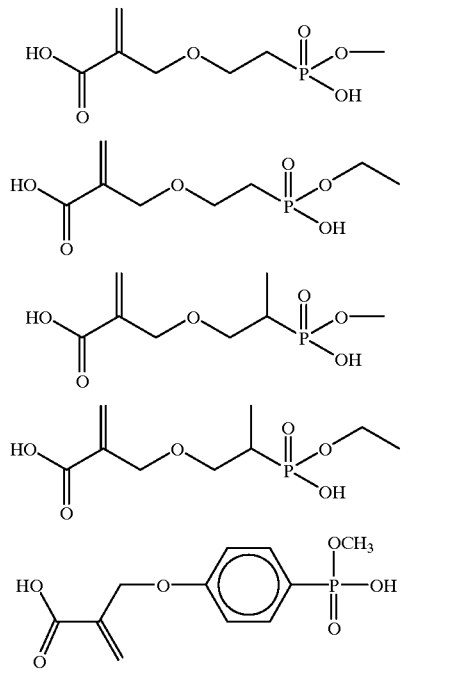

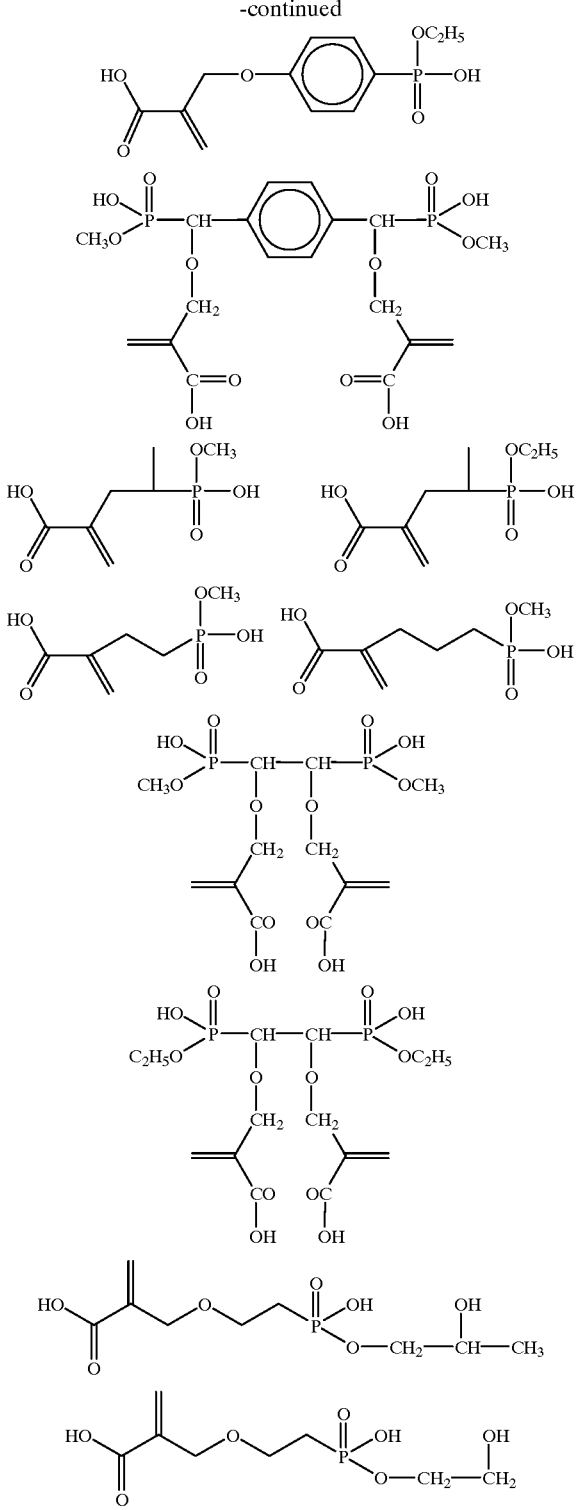

Compared with the corresponding acrylophosphonic acid monoesters according to the invention acrylophosphonic acid monoesters according to the invention are much better soluble in mixtures of polar organic solvents, such as methanol, ethanol, isopropanol, methyl ethyl ketone, acetone, ethyl acetate, dimethylformamide or dimethyl sulfoxide, and water, but also have a high solubility in the polar organic solvents themselves.

In order to achieve a sufficient adhesion to enamel and dentine of dental materials, the enamel edges and the dentine are normally etched with 35 to 40% phosphoric acid for approx 20 to 30 seconds each time after the preparation of for example a cavity. Surprisingly, the acrylophosphonic acid monoesters according to the invention have a clearly higher acidity compared with the corresponding acrylophosphonic acids and thus a greater self-etching effect on enamel and dentine, so that an additional etching of enamel and dentine can be avoided.

Due to the presence of polymerizable groups, the acrylophosphonic acid esters according to the invention are suitable as starting materials for the preparation of polymers and copolymers. They can be homopolymerized with the known methods of radical polymerisation or copolymerized e.g. with suitable comonomers.

To carry out the polymerisation, the known radical initiators (cf. Encyclopedia of Polymer Science and Engineering, Vol. 13, Wiley-Interscience Publisher, New York 1988, 754 et seq) can be used. Azo compounds, such as azobis(isobutyronitrile) (AIBN) or azobis-(4-cyanovalerianic acid) or peroxides, such as dibenzoylperoxide, dilauroylperoxide, tert.-butylperoctoate, tert.-butylperbenzoate or di.-(tert.-butyl)-peroxide are particularly suitable.

Benzopinacol and 2,2'-dialkylbenzopinacols are also suitable as initiators for hot-curing.

Furthermore, photoinitiators (cf. J. P. Fouassier, J. F. Rabek (Ed.), Radiation Curing in Polymer Science and Technology, Vol. II, Elsevier Applied Science, London and New York 1993) can also be used for polymerisation with UV light or light of visible wavelengths, such as benzoinethers, dialkylbenzilketals, dialkoxyacetophenones, acylphosphinic oxides, α-diketones, such as 9,10-phenanthrenequinone, diacetyl, furil, anisil, 4,4'-dichlorobenzil and 4,4'-dialkoxybenzil, and camphorquinone.

The acrylophosphonic acid monoesters according to the invention can be used in particular as a component of adhesives, cements, composites and molded articles as well as, preferably, dental materials. The acrylophosphonic acid monoesters according to the invention can also be used in polymerized or partly polymerized form i.e. in the form of polymers such as homo- or copolymers, for example as a component of glass ionomer cements.

The acrylophosphonic acid monoesters according to the invention can be polymerized alone or in a mixture with conventional radically polymerizable comonomers, in particular with difunctional crosslinking monomers. Crosslinking bi- or multifunctional acrylates or methacrylates, such as e.g. bisphenol-A-di-(meth)acrylate, bis-GMA (the addition product of methacrylic acid and bisphenol-A-diglycidyl ether), UDMA (the addition product of hydroxyethyl methacrylate and 2,2,4-trimethylhexamethylene diisocyanate), di-, tri- or tetraethylene glycol di(meth)acrylate, trimethylolpropantri(meth)acrylate and pentaerythritol tetra(meth)acrylate above all are suitable for the preparation of adhesives or dental materials. Butane diol di(meth)acrylate, 1,10-decane diol di(meth)acrylate and 1,12-dodecanediol di(meth)acrylate which are accessible by esterifying (meth)acrylic acid with the corresponding diols are also suitable.

The acrylophosphonic acid monoesters according to the invention can be used in free form or in the form of their salts, i.e. as phosphonate esters. In the case of the salts alkali-metal ions, in particular sodium and lithium ions, as well as organic ammonium ions, in particular those derived from amine accelerators such as N,N-dihydroxyethyl-p-toluidine, N,N-bis-(2-hydroxy-3-methacryloxypropyl-3,5-xylidine or 4-(dimethylamino)-benzoic acid-2-ethyl-hexylester are preferably used as counterions. Amine accelerators are used in the field of dentistry as a component for example of photoinitiator systems. In general they are tert. amines which can act as H-donators and thus accelerate radical generation (cf. L. A. Linden, "Photocuring of Polymeric Dental Materials and Plastic Composite Resins" in Radiation Curing in Polymer Science and Technology, Vol. IV, J. P. Fouassier, J. F. Rabek (Editors), Elsevier Appl.Sci., London, New York 1993, 396 et seq).

Moreover, the acrylophosphonic acid monoesters according to the invention or their mixtures with other radically polymerizable comonomers can be filled with organic or inorganic particles or fibres to improve the mechanical properties. Preferred inorganic particulate fillers are amorphous spherical materials based on mixed oxides of $SiO_2$, $ZrO_2$ and/or $TiO_2$, microfine fillers, such as pyrogenic silicic acid or precipitation silicic acid, as well as macro- or minifillers, such as quartz, glass ceramic or glass powders with an average particle size of 0.01 to 5 μm. Furthermore, x-ray opaque fillers, such as ytterbium trifluoride, or glass fibres, polyamide or carbon fibres can also be used.

If necessary, further components can be added to the acrylophosphonic acid monoesters or mixtures thereof, above all solvents, such as water, methanol, ethanol, isopropanol, methyl ethyl ketone, acetone, ethyl acetate, dimethylformamide, dimethyl sulfoxide or mixtures thereof, as well as stabilisers, UV-absorbers, dyes, pigments or lubricants. Water, ethanol, acetone and ethyl acetate as well as mixtures thereof are preferred as solvents for use in dental materials.

The acrylophosphonic acid monoesters according to the invention are suitable in particular as a component of dental materials, such as fixing cements and filler composites and above all dental adhesives. Such materials are characterized by a very good adhesion to different substrates, such as hard tooth substance and metallic substrates, and are hydrolysis-stable under moist conditions.

Preferred dental materials according to the invention contain the following components (a), (b), (c), (d) and/or (e):
(a) 0.5 to 99 wt.-%, preferably 10 to 80 wt.-% and particularly preferably 20 to 50 wt.-% of acrylophosphonic acid monoesters according to the invention,
(b) 0.01 to 5 wt.-% and preferably 0.1 to 2.0 wt.-% of radical initiators,
(c) 0 to 80 wt.-%, preferably 0 to 60 wt.-% and particularly preferably 0 to 50 wt.-% radically polymerizable comonomers,
(d) 0 to 95 wt.-%, preferably 0 to 80 wt.-% and particularly preferably 0 to 70 wt.-% solvents, in particular water, ethanol, acetone, ethyl acetate or mixtures thereof as well as mixtures of water with the named organic solvents,
(e) 0 to 90 wt.-%, particularly preferably, depending on the application, 0 to 20 wt.-% (adhesive), 20 to 60 wt.-% (cement) and 60 to 85 wt.-% (filling composite) filler.

According to a particularly preferred embodiment, the dental materials according to the invention are free from acrylophosphonic acids such as are described by way of e.g. in DE 197 46 708.

The invention is explained in more detail in the following examples.

EXAMPLES

Example 1

2-[4-(hydroxymethoxyphosphoryl)-oxa-butyl]-acrylic acid (1)

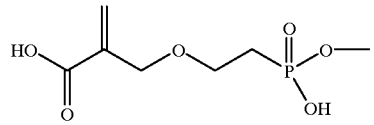

133 g (0.5 mol) 2-[4-(dimethoxyphosphoryl)-2-oxa-butyl]-acrylic acid ethyl ester which is accessible by the reaction of 2-hydroxyethylphosphonic acid diethyl ester with α-chloromethylacrylic acid ethyl ester (N. Moszner, F. Zeuner, U. K. Fischer, V. Rheinberger, Macromol. Chem. Phys. 200 (1999) 1062), are added dropwise to a solution of 120 g (3.0 mol) NaOH in 1200 ml water accompanied by ice-cooling so that the temperature does not exceed 25° C. Then the reaction mixture is adjusted to a pH of 1 with approx. 260 ml concentrated hydrochloric acid. The product is washed three times with 500 ml of methylene chloride each time, the remaining aqueous phase is then saturated with sodium chloride and subsequently filtered. The filtrate is extracted three times with 500 ml of tetrahydrofuran each time. After the combined extracts have been dried over anhydrous $Na_2SO_4$, the product is concentrated on the rotary evaporator (40 mbar, 50° C.) and the oily residue dried over phosphorous pentoxide in the desiccator until its weight is constant. 93.6 g (86% yield) of a colourless powder remain, which melts in the range between 71–75° C.

IR (KBr, $cm^{-1}$): 672 (m), 751 (m), 780 (m), 825 (s), 911 (m), 946 (m), 969 (s), 998 (s), 1014 (s), 1027 (s), 1044 (s), 1055 (s), 1063 (s), 1124 (s), 1188 (m), 1210 (m), 1311 (m), 1372 (w), 1393 (m), 1428 (w), 1448 (m), 1456 (m), 1487 (w), 1634 (s), 1678 (s), 2598 (w), 2672 (w), 2870 (m) and 2900–3200 (b).

$^1$H-NMR (400 MHz, DMSO-$d_6$, ppm): 1.95–2.05 (m, 2H, $CH_2P$), 3.53–3.65 (m, 5H, $OCH_2CH_2$), 4.08 (s, 2H, =C—$CH_2$O), 5.82 and 6.13 (s, 2×1H,$CH_2$=C), 10.5 (b, 2H, OH).

$^{13}$C-NMR (100 MHz. DMSO-$d_6$, ppm): 26.09 and 27.44 (d; $CH_2P$), 51.56 ($CH_3$), 64.76 (O$\underline{C}H_2CH_2$), 68.59 (=C—$\underline{C}H_2$O), 125.26 ($CH_2$=), 138.20 ($\underline{C}$=$CH_2$), 167.11 (C=O).

$^{31}$P-NMR (161.9 MHz, DMSO-$d_6$): 26.05.

Example 2

Radical Homopolymerization of Monomer (1)

2.24 g (10.0 mmol) monomer 1 and 2.0 mol-% azobis (isobutyronitrile), relative to monomer, were dissolved in 7.7 ml of dimethylformamide in a Schlenk-receptacle. The monomer solution was degassed by repeated freezing under argon and thawing under a fine vacuum and subsequently polymerized under argon at 65° C. During the polymerisation, the viscosity of the starting solution increases perceptibly. After one hour, the highly-viscous solution is precipitated by pouring into 10 times the quantity of tetrahydrofuran and, after the colourless polymer powder is dried until its weight is constant, a monomer conversion of 40.1 % is determined.

Example 3

Investigation of the Hydrolytic Stability of Monomer 1

Monomer 1 is dissolved in a 1:1 mixture of water and ethanol and a 20% solution is stored at 37° C. The $^1$H-NMR spectrum of the solution is recorded weekly. During the 8-week investigation period, there was no change in the spectrum of monomer 1, which shows its hydrolytic stability.

Example 4

Investigation of the Adhesion to Enamel of Monomer 1

An adhesive of the following composition (amounts in weight-%) was prepared to investigate the adhesion to enamel on bovine tooth enamel:

Monomer 1: 17.4%

Glycerine dimethacrylate: 38.2%

2-hydroxyethyl methacrylate: 26.3%

Water: 17.3%

Photoinitiator: 0.8%

Bovine teeth are embedded in plastic cylinders so that the enamel zone and the plastic are located on one level. After 15 seconds' of etching with 37% phosphoric acid thorough rinsing is carried out with water. Then a layer of adhesive of the above composition is painted on with a microbrush, blown on briefly with the air blower to remove the solvent and lit for 40 seconds with a halogen lamp (Astralis 7, Vivadent). A composite cylinder made of Tetric® Ceram (Vivadent) is polymerized onto the adhesive layer in two layers of 1–2 mm each. Subsequently the testpieces are stored in water for 24 hours at 37° C. and the adhesive strength is subsequently determined. A value of 14.0 MPa is recorded.

Example 5

Investigation of the Solubility and Acid Strength of Monomer 1

The solubility of monomer 1 in water and ethanol was determined and the pH value of a 20% solution of the monomer in a 1:1 mixture of ethanol and water measured. The results were compared with the values of a structurally analogous phosphonic acid and are listed in Table 1.

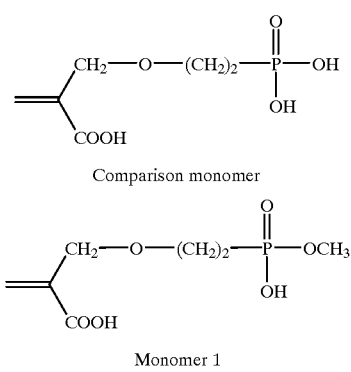

Comparison monomer

Monomer 1

The results show that monomer 1 is clearly better soluble in organic solvents such as ethanol and more strongly acid, than the comparison monomer.

The higher acidity of the monomer according to the invention is also expressed in its etching capacity vis-à-vis tooth enamel. A 40% aqueous solution of monomer 1 thus produces after only 10 seconds on bovine tooth enamel an etching pattern which is clearly visible under a scanning electron microscope, whereas in the case of the corresponding phosphonic acid 30 seconds' exposure time are required to achieve the same etching effect.

Such clear differences in the solution behaviour and in the etching effect were not to be expected given the small structural difference between monomer 1 and the comparison compound (exchange of an $OCH_3$ group for an $OH$ group).

TABLE 1

Comparison of the properties of phosphonic acid and phosphonic acid monoester

| Parameter | Comparison monomer | Monomer 1 |
| --- | --- | --- |
| water solubility | approx 40 g/dl | >50 g/dl |
| solubility in ethanol | practically insoluble | >50 g/dl |
| pH value of a 20% aqueous solution | 1.25 | 0.61 |

What is claimed is:

1. Acrylophosphonic acid monoesters of the general formula (I), stereoisomers thereof or mixtures of these

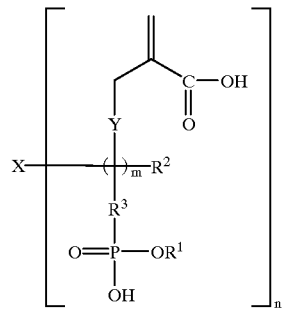

in which $R^1$, $R^2$, $R^3$, X, Y, m and n have the following meanings:

$R^1$ = a linear or branched $C_1$ to $C_{20}$ alkyl or $C_6$ to $C_{14}$ aryl radical;

$R^2$ = hydrogen, a linear or branched $C_1$ to $C_5$ alkyl or phenyl radical;

$R^3$ = a linear or branched $C_1$ to $C_5$ alkylene radical, phenylene or is absent;

Y oxygen, $C_1$ to $C_8$ alkylene or is absent;

m = 0 or 1;

n = 1 or 2;

provided that Y=0, m=0 and $R^3$=absent cannot be true at the same time and further provided that for m=1 and n=1

X hydrogen or a linear or branched $C_1$ to $C_3$ alkyl radical or a $C_6$ to $C_{14}$ aryl radical;

for m=1 and n=2

X = a linear or branched $C_1$ to $C_{10}$ alkylene, $C_6$ to $C_{10}$ arylene, $C_7$ to $C_{20}$ arylalkylene radical or a chemical bond which links together two radicals with the structure of formula (I) in brackets, the individual radicals being able to be substituted or unsubstituted.

2. Acrylophosphonic acid monoesters according to claim 1, wherein the variables of formula (I) have the following meanings independently of each other:

$R^1$=a linear or branched $C_1$ to $C_{10}$ alkyl or phenyl radical;

$R^2$=hydrogen or a linear or branched $C_1$ to $C_3$ alkyl radical;

$R^3$=a linear or branched $C_1$ to $C_4$ alkylene radical, phenylene or is absent;

Y=oxygen or is absent; and

X=hydrogen or a linear or branched $C_1$ to $C_3$ alkyl radical (for m=1 and n=1); or X=a linear or branched $C_1$ to $C_6$ alkylene radical, phenylene or a chemical bond which links together two radicals with the structure of formula (I) in brackets (for m=I and n=2).

3. Acrylophosphonic acid monoesters according to claim 2, wherein the variables of formula (I) have the following meanings independently of each other:

$R^1$=a linear or branched $C_1$ to $C_4$ alkyl radical, which can be unsubstituted or can be substituted by an OH group;

$R^2$=hydrogen or a linear or branched $C_1$ to $C_3$ alkyl radical;

$R^3$=a linear or branched $C_1$ to $C_4$ alkylene radical, phenylene or is absent;

Y oxygen or is absent.

4. Acrylophosphonic acid monoesters according to claim 1, wherein m=0 or for m=1, n=2, and X=phenylene or a chemical bond which joins together two radicals with the structure of formula (I) in brackets.

5. Acrylophosphonic acid monoesters according to claim 1, wherein said acrylophosphonic acid monoester is a component of an adhesive, of a polymer, of a composite, of a cement, of a molded article or a dental material.

6. Acrylophosphonic acid monoesters according to claim 5, wherein the dental material is a dental adhesive, a fixing cement or a filling composite.

7. Acrylophosphonic acid monoesters according to claim 5, wherein the acrylophosphonic acid monoester is present in at least partially polymerized form.

8. Dental material containing an acrylophosphonic acid monoester according to claim 1.

9. Dental material according to claim 8, containing the acrylophosphonic acid monoester in at least partially polymerized form.

10. Polymers and copolymers obtained by polymerization or copolymerization of an acrylophosphonic acid monoester according to claim 1.

* * * * *